United States Patent [19]

Goodnow et al.

[11] 4,300,545

[45] Nov. 17, 1981

[54] METHOD AND NOZZLE FOR NASAL VACCINATION OF IMMATURE MAMMALS

[75] Inventors: Robert A. Goodnow; Floyd J. Shade; Thomas A. Sloboth; Donald J. Kaye, all of Omaha, Nebr.

[73] Assignee: Schering Corporation, Kenilworth, N.J.

[21] Appl. No.: 161,997

[22] Filed: Jun. 23, 1980

[51] Int. Cl.[3] ........................ A61D 7/00; A61M 11/06

[52] U.S. Cl. .............................. 128/200.14; 128/239; 128/230; 128/253

[58] Field of Search ............... 128/239, 241, 242, 245, 128/250, 207.18, 225, 151, 207.28, 152, 747, 765, 760, 772, 223, 232, 248, 233, 234, 253, 230, 203.15, 200.14; 239/589

[56] References Cited

U.S. PATENT DOCUMENTS

| | | | |
|---|---|---|---|
| 128,257 | 6/1872 | Snyder | 128/239 |
| 991,022 | 5/1911 | Rees et al. | 128/232 |
| 1,856,811 | 5/1932 | Inaki | 128/250 |
| 1,958,085 | 5/1934 | Hammon | 239/589 |
| 2,255,833 | 9/1941 | Taylor | 128/232 |
| 2,434,875 | 1/1948 | Turnbull et al. | 128/250 |
| 2,612,894 | 10/1952 | Akins | 128/250 |
| 3,415,248 | 12/1968 | Scott | 128/245 |
| 3,648,695 | 3/1972 | Bowen | 128/225 |
| 3,820,698 | 6/1974 | Franz | 128/250 |
| 3,857,423 | 12/1974 | Ronca, Jr. | 141/5 |
| 4,122,841 | 10/1978 | Rock et al. | 128/151 X |
| 4,127,126 | 11/1978 | Schunk | 128/234 |

FOREIGN PATENT DOCUMENTS

| | | | |
|---|---|---|---|
| 166171 | 3/1905 | Fed. Rep. of Germany | 128/207.18 |
| 6707 | of 1909 | United Kingdom | 128/250 |

OTHER PUBLICATIONS

Sisson, "The Anatomy of the Domestic Animals", 1941, pp. 558-560.

*Primary Examiner*—Henry J. Recla

*Attorney, Agent, or Firm*—Warrick E. Lee, Jr.; Vincent H. Gifford; Bruce M. Eisen

[57] ABSTRACT

Method and means for vaccinating a mammal using a convex nozzle with an elongated tip. The mammal's alar fold is pushed aside by the tip so that vaccine is deposited behind the alar fold. Vaccine is then dispensed through the nozzle.

12 Claims, 10 Drawing Figures

METHOD AND NOZZLE FOR NASAL VACCINATION OF IMMATURE MAMMALS

BACKGROUND

This invention relates, in general, to the vaccination of mammals, more specifically to method and means for depositing a preselected amount of vaccine within the nasal passage of an immature mammal.

Prior art devices such as aerosol sprays, a standard syringe (with or without an attached needle), pump sprays, and atomizers are not always able to administer nasal vaccine safely and effectively. The present invention is predicated upon recognition that immature mammals have a pronounced alar fold partially blocking their nasal passageways and a method and means for solving this previously-unrecognized problem.

SUMMARY OF THE INVENTION

The present invention provides an improved method and nozzle for nasal vaccination of immature animals.

One aspect of the present invention is a method of safely and effectively vaccinating a mammal having an alar fold comprising the steps of:

a. inserting into a nostril of the mammal a convex nozzle having an elongated tip,
b. pushing the mammal's alar fold aside with the elongated tip. p1 c. dispensing a preselected amount of vaccine from a container through the nozzle while the alar fold is pushed aside by the tip such that vaccine is deposited behind the alar fold, and
d. withdrawing the nozzle from the nostril of the mammal.

A second aspect of the invention is a nasal nozzle for insertion into the nasal cavities of mammals having alar folds for introducing fluid pharmaceutical composition comprising:

(a) a convex body continuously curving at radius of 0.5 to 1.0 inches from a wide portion to an apex, said convex body having an axis, the axial length of said convex body being 0.36 to 0.6 inches, the diameter of said wide portion measured perpendicular to said axis being 0.48 to 0.6 inches.
(b) elongated tip means for pushing aside the alar fold of the mammal upon insertion of said nozzle into the nasal cavity projecting from said apex along said axis, said tip means having length of 0.12 to 0.24 inches and outside diameter of 0.05 to 0.20 inches.
(c) a channel throughout said convex body and elongated tip means along said axis, said channel having decreasing area from a rear end of said channel to an outlet opening on an end of said elongated tip means, said outlet opening having diameter of 0.025 to 0.05 inches, said channel having non-uniform taper and having a rear section having uniform taper, an offset wherein the angle included between said offset and said axis is from 25° to 45°, and a front section having uniform taper such that the cross-sectional area of said front section decreases by 25% to 45% per ¼ inch of front section length, and
(d) adapting means for attaching said nozzle to a container for dispensing a pharmaceutical composition through said channel.

The invention is particularly effective when used on 1 to 6 week old canine puppies, 1 to 6 week old kittens, 1 to 10 day old piglets, and 4 to 10 week old rabbits. Preferably the length of the elongated tip will be from 0.12 to 0.24 inches.

The improved nozzle of this invention has been found to be particularly effective for administering vaccine suspension having a solids content of 40–60 percent.

An example of a commercially available nasal vaccine is sold under the tradename INTRA-TRAC I by Burns-Biotec Laboratories, Inc., Omaha, Nebr. Of course, other vaccines suitable for nasal administration may be used.

DETAILED DESCRIPTION OF THE INVENTION

Figure 1:
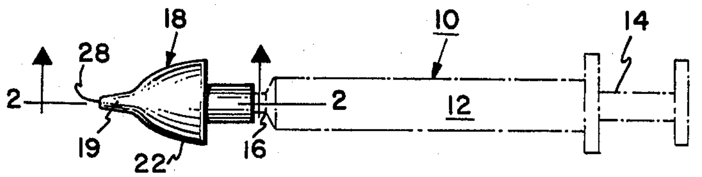
FIG. 1 is a cross-section of a standard syringe with a preferred nasal nozzle of this invention incorporated thereon.

Referring to FIGS. 1, 2, 3, and 4 there is illustrated a standard syringe 10 comprising a reservoir 12, a plunger 14 and a hub 16. Nozzle 18 is fitted to hub 16. Nozzle 18 comprises a generally convex body 22 having an elongated essentially cylindrical tip portion 19 and a neck portion 20 which mates with the hub of the syringe.

Nozzle 18 has a longitudinal channel 24 (see FIG. 2) which decreases in cross-sectional area from the rear opening 26 to the outlet orifice 28. This decrease in area causes a pressure drop in fluid vaccine as it flows through the opening, which is believed to cause turbulence which in turn causes the vaccine to scatter into smal drops as it leaves outlet orifice 28. The scattered drops are deposited over a large surface within the mammals nasal passage, thereby preventing the vaccine from being swallowed or from flowing out of the mammals nose after the nozzle is removed. In the preferred embodiment an offset 29 is believed to cause increased turbulence, hence, increased scattering. Surprisingly, the scattered drops do not cause the mammal to sneeze.

The convex body 22 is preferably in the form of a resilient tent-like projection for use with small young animals.

The size and shape of nozzle 18 is very important. Preferred dimensions (with the most preferred in parenthesis) of the nozzle are shown in Table I. All dimensions are in inches unless otherwise specified.

TABLE I

| | |
|---|---|
| Length of Tip 19: | 0.12 to 0.24 (0.22) |
| Diameter of bore at outlet 28: | 0.025 to 0.05 (0.04) |
| Outside diameter of Tip 19: | 0.05 to 0.20 (0.10) |
| Radius of curvature for convex Body 22: | 0.5 to 1.0 (0.75) |
| Diameter of convex Body 22 at widest portion 17: | 0.48 to 0.6 (0.55) |
| Axial Length of Body 22 (dimension 40, FIG. 2): | 0.36 to 0.6 (0.48) |
| Ratio of channel Area A to Area B (FIG. 2): | Ratio of 1.05:1 to 1.15:1 (1.1:1) |
| Angle included between Offset 29 and Longitudinal direction: | 25° to 45° (35°) |
| Decrease in Area along forward portion 24B of Channel 24: | 25%/quarter inch to 45%/quarter inch (35%/quarter inch) |
| Length of rear bore 24A: | 0.44 to 0.74 (0.59) |
| Length of Front bore 24B: | 0.22 to 0.37 (0.295) |
| Diameter of rear most part of rear bore (at A): | 0.94 to 0.19 (0.125) |

The decrease in area along forward portion 24B of channel 24 is not absolutely necessary, but preferred. Acceptable results will be attained so long as channel 24 decreases in area some place between its inlet and outlet.

It is preferable that the nasal nozzle be made of plastic with convex Body 22 in the form of a tent-like projection that is somewhat pliable. This can be very useful in utilizing the plastic nasal nozzle on small young animals whose nasal tissues are very delicate and vary in size. By utilizing the proper size for the plastic nasal nozzle 18, it can be inserted into the nares of the small, young animals until a light sealing condition is created which enables better distribution of vaccines as they emerge as scattered droplets from the orifice 28 of the nozzle.

Figure 5:
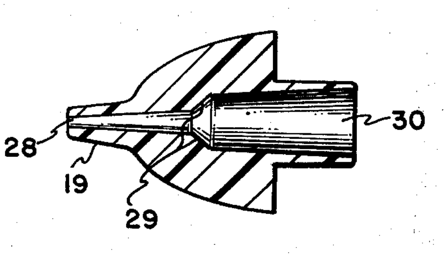
FIG. 5 is modification of the plastic nasal nozzle shown in FIG. 2.

FIG. 5 shows a modification of the plastic nasal nozzle of this invention wherein the convex body is solid instead of tent like and wherein the longitudinal passageway 30 is somewhat larger.

Figure 2:
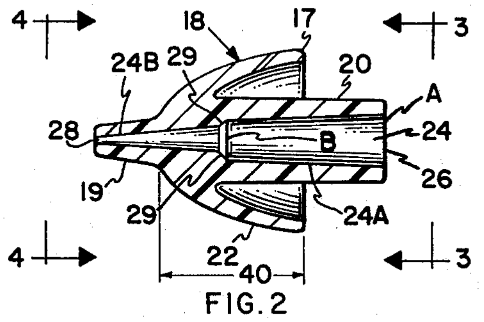
FIG. 2 is a cross-section of the FIG. 1 nozzle taken along the lines 2—2.
Figure 3:
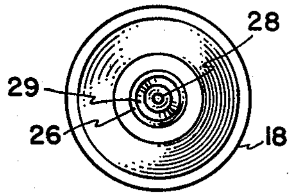
FIG. 3 is a rear view of the FIG. 1 nozzle taken along the lines 3—3 of FIG. 2.
Figure 4:
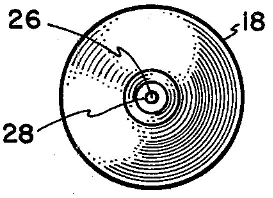
FIG. 4 is a front view of the FIG. 1 nozzle taken along lines 4—4 of FIG. 2.
Figure 6:
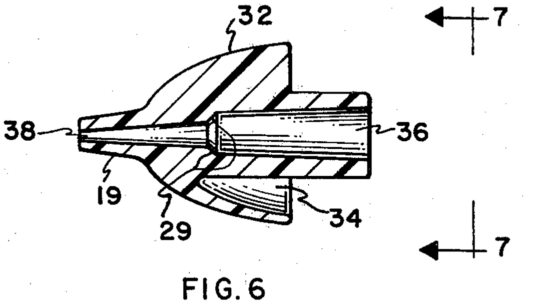
FIG. 6 is another modification of the nasal nozzle.
Figure 7:
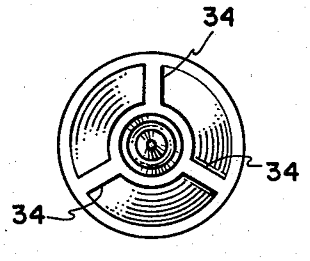
FIG. 7 is a rear view of the FIG. 6 nozzle taken along lines 7—7 of FIG. 6, showing a ribbed structure.

FIGS. 6 and 7 show a further modification of the nasal nozzle of this invention wherein the nasal nozzle 32 is in the form of a tent like structure as disclosed in FIG. 2, but which contains ribs 34 (see FIG. 7) to help rigidify the structure. By choosing materials of construction having different degrees of rigidity and by varying the number of ribs, nozzles of any desired degree of pliability may be constructed.

The plastic compositions which may be used in the practice of this invention are the well known plastic materials such as polyolefins, including high density polyethene, low density polyethelene and polypropylene, which is preferred. Other plastic materials may be used such as rubber compositions, polymers and copolymers of styrene, soft nylons, polyvinylchloride compositions, and even harder materials such as impact polystyrene and polycarbonates.

Figure 8:
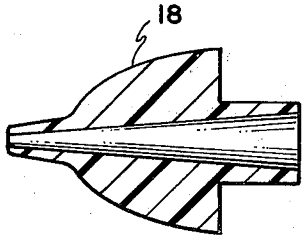
FIG. 8 is a cross-sectional view of an alternate embodiment of the nozzle.

FIG. 8 is a longitudinal view of a nozzle of the invention having a channel of uniform taper. This type of channel, while not preferred, will still produce acceptable results.

Figure 9:
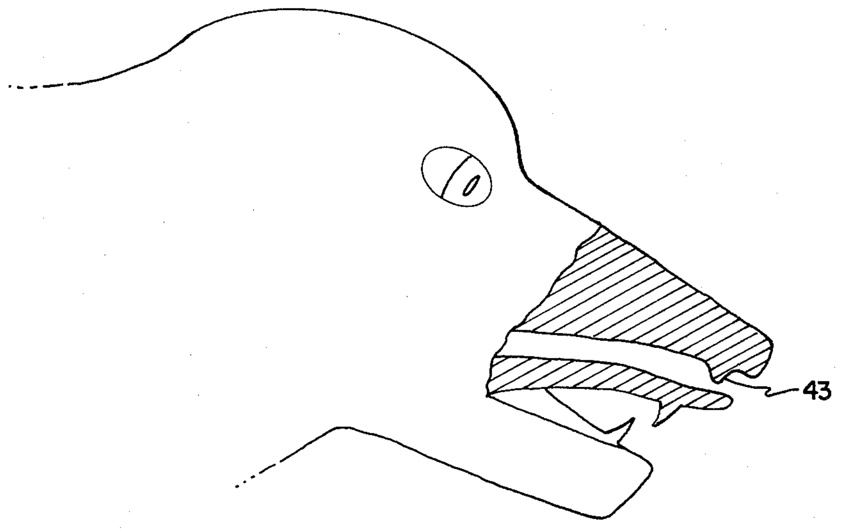
FIG. 9 is a schematic partial sectional view of a mammal's nasal passageway showing the alar fold.
Figure 10:
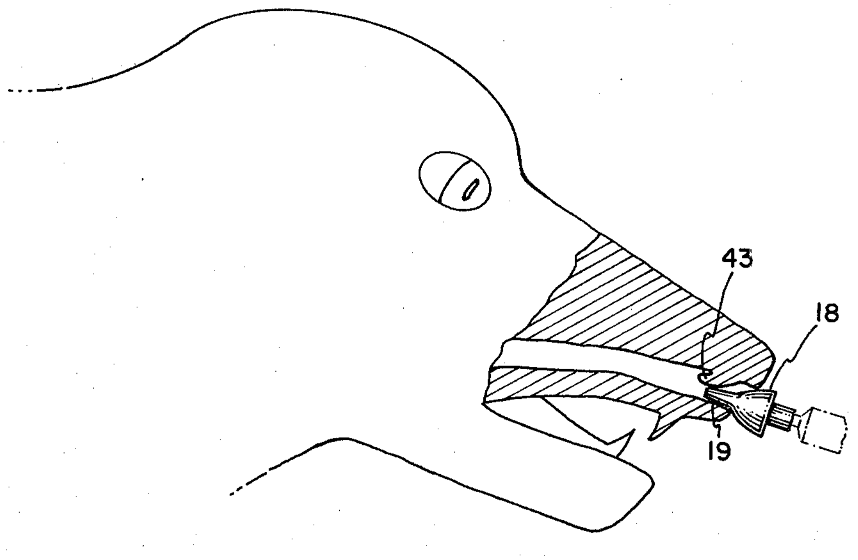
FIG. 10 is a schematic partial sectional view of a mammal's nasal passageway showing a nozzle of the present invention correctly inserted for dispensing vaccine.

FIG. 9 is a schematic partial sectional view of a mammal's nasal passageway. Alar fold 43 partially obstructs the passage, causing nasal vaccination with prior-art devices to be difficult. Furthermore, when young animals are handled, they often constrict their nostrils, adding to the problem. In immature swine, the alar fold is pronounced, blocking about 40 percent of the nasal passageway. In puppies and kittens, the alar fold is even more pronounced, blocking about 50% of the nasal passage. Sisson et al, in *The Anatomy of the Domestic Animals* (W. B. Saunders Company, 1941) in FIG. 489, page 559, shows the alar fold to be not nearly the obstacle to nasal vaccination that it actually is. FIG. 10 is a schematic partial sectional view of a mammal's nasal passageway showing a nozzle 18 of the present invention correctly inserted for dispensing a vaccine. Nozzle 18 is inserted into the mammal's nostril. Elongated tip 19 pushes alar fold 43 aside, and is inserted such that vaccine will be deposited behind the alar fold. With the nozzle so inserted, a preselected amount of vaccine is dispensed from a syringe. After the vaccine is dispensed, the nozzle is, of course, withdrawn from the mammal's nostril.

In 1 to 10 day old piglets, the alar fold is an obstacle to vaccination. As the piglet matures, the nasal passage opens up, i.e., the alar fold is no longer an obstacle to vaccinations. In 1 to 6 week old puppies, 1 to 6 week old kittens, and 4 to 10 week old rabbits, the alar fold is an obstacle to vaccination. As these animals mature the alar fold remains an obstacle, hence this invention is useful in nasally vaccinating dogs, cats, and rabbits at any age.

What is claimed is:

1. A nasal nozzle for insertion into the nasal cavities of mammals having alar folds for introducing fluid pharmaceutical composition comprising:

(a) a convex body continuously curving at radius of 0.5 to 1.0 inches from a wide portion to an apex, said convex body having an axis, the axial length of said convex body being 0.36 to 0.6 inches, the diameter of said wide portion measured perpendicular to said axis being 0.48 to 0.6 inches, (b) elongated tip means for pushing aside the alar fold of the mammal upon insertion of said nozzle into the nasal cavity projecting from said apex along said axis, said tip means having length of 0.12 to 0.24 inches and outside diameter of 0.05 to 0.20 inches, (c) a channel throughout said convex body and elongated tip means along said axis, said channel having decreasing area from a rear end of said channel to an outlet opening on an end of said elongated tip means, said outlet opening having diameter of 0.025 to 0.05 inches, said channel having non-uniform taper and having a rear section having uniform taper, an offset wherein the angle included between said offset and said axis is from 25° to 45°, and a front section having uniform taper such that the cross-sectional area of said front section decreases by 25% to 45% per ¼ inch of front section length, and (d) adapting means for attaching said nozzle to a container for dispensing a pharmaceutical composition through said channel.

2. The combination of the nozzle of claim 1 attached to a container of vaccine.

3. The combination of claim 2 wherein the container is a syringe.

4. The nozzle of claim 1 wherein said adapting means are adapted to fit a syringe of the type having a hub, reservoir, and plunger.

5. A method of safely and effectively vaccinating a mammal haing an alar fold comprising the steps of:

a. inserting into a nostril of the animal a nozzle having an elongated tip, b. pushing the mammal's alar fold aside with said elongated tip, c. dispensing a preselected amount of vaccine from a container through said nozzle while the alar fold is pushed aside by said tip such that vaccine is deposited behind the alar fold, and d. withdrawing the nozzle from the nostril of said mammal.

6. The method of claim 5 wherein said container is a syringe.

7. The method of claim 5 wherein the mammal is a 1 to 6 week old canine puppy.

8. The method of claim 5 wherein the mammal is a 1 to 6 week old kitten.

9. The method of claim 5 wherein the mammal is a 1 to 10 day old piglet.

10. The method of claim 5 wherein the mammal is a 4 to 10 week old rabbit.

11. The method of claim 5 wherein said vaccine is a suspension.

12. The method of claim 1 wherein said suspension has solid content of 40 to 60 weight percent.

* * * * *